(12) United States Patent
Setou et al.

(10) Patent No.: US 8,743,138 B2
(45) Date of Patent: Jun. 3, 2014

(54) METHOD AND SYSTEM FOR PROCESSING MASS ANALYSIS DATA

(75) Inventors: Mitsutoshi Setou, Hamamatsu (JP); Shigeki Kajihara, Uji (JP)

(73) Assignee: Shimadzu Corporation, Kyoto-Shi (JP)

( * ) Notice: Subject to any disclaimer, the term of this patent is extended or adjusted under 35 U.S.C. 154(b) by 214 days.

(21) Appl. No.: 13/305,535

(22) Filed: Nov. 28, 2011

(65) Prior Publication Data

US 2012/0133671 A1    May 31, 2012

(30) Foreign Application Priority Data

Nov. 29, 2010 (JP) ................................. 2010-264751

(51) Int. Cl.
*G09G 5/02* (2006.01)
*G06K 9/00* (2006.01)

(52) U.S. Cl.
USPC ......................................... 345/593; 382/128

(58) Field of Classification Search
USPC .......................................... 382/128; 345/593
See application file for complete search history.

(56) References Cited

U.S. PATENT DOCUMENTS

| 7,123,750 | B2 * | 10/2006 | Lu et al. ........................ 382/110 |
| 7,187,800 | B2 * | 3/2007 | Hibbard ........................ 382/173 |
| 7,425,700 | B2 * | 9/2008 | Stults et al. .................... 250/288 |
| 7,676,442 | B2 * | 3/2010 | Ben-Hur et al. ................. 706/45 |
| 2008/0017793 | A1 * | 1/2008 | James et al. ................... 250/288 |
| 2008/0118181 | A1 * | 5/2008 | Potuluri et al. ............... 382/275 |

FOREIGN PATENT DOCUMENTS

| JP | 2007-066533 | 3/2007 |
| JP | 2007-157353 | 6/2007 |
| JP | 2007-257851 | 10/2007 |

OTHER PUBLICATIONS

Kiyoshi Ogawa et al., "Research and Development of Mass Microscope", Shimadzu Review, Mar. 31, 2006, vol. 62, Nos. 3-4, pp. 125-135.
Takahiro Harada et al., "Biological Tissue Analysis Using Mass Microscope", Shimadzu Review, Apr. 24, 2008, vol. 64, Nos. 3-4, pp. 139-146.
Search for Biomarkers on Pathological Samples Using MS Imaging Technology, Shimadzu Corporation, Oct. 8, 2010, http://www.an.shimadzu.co.jp/bio/biomarker/297-0425_msimaging.pdf.
Morinaga et al., "Development of the Software Using Principal Component Analysis for MS Imaging Data", Abstract of the 57th Annual Conference on Mass Spectrometry 2009, The Mass Spectrometry Society of Japan, May 1, 2009, pp. 174-175.

* cited by examiner

*Primary Examiner* — Kee M Tung
*Assistant Examiner* — Nicholas R Wilson
(74) *Attorney, Agent, or Firm* — Bingham McCutchen LLP

(57) ABSTRACT

In an imaging mass analysis, image information of a sample allows users to grasp specific information about the sample, such as distribution of a portion with a particular function or effect. The mass spectrum intensity data are normalized for each pixel so that the sum of the intensities over the entire mass-to-charge ratio (m/z) is one. Entropy is calculated by totaling the product of the intensity normalizing at each m/z and the logarithm of that intensity over the entire m/z range. After the entropy is calculated for each pixel, the pixels are colored according to their entropy values to display a two-dimensional color image of entropy distribution. The entropy of a cancerous portion is relatively small because of a high content of a specific kind of substance and the simplified composition of the substances. Thus, the cancerous part and the normal part of the entropy image can be distinguished.

6 Claims, 7 Drawing Sheets
(5 of 7 Drawing Sheet(s) Filed in Color)

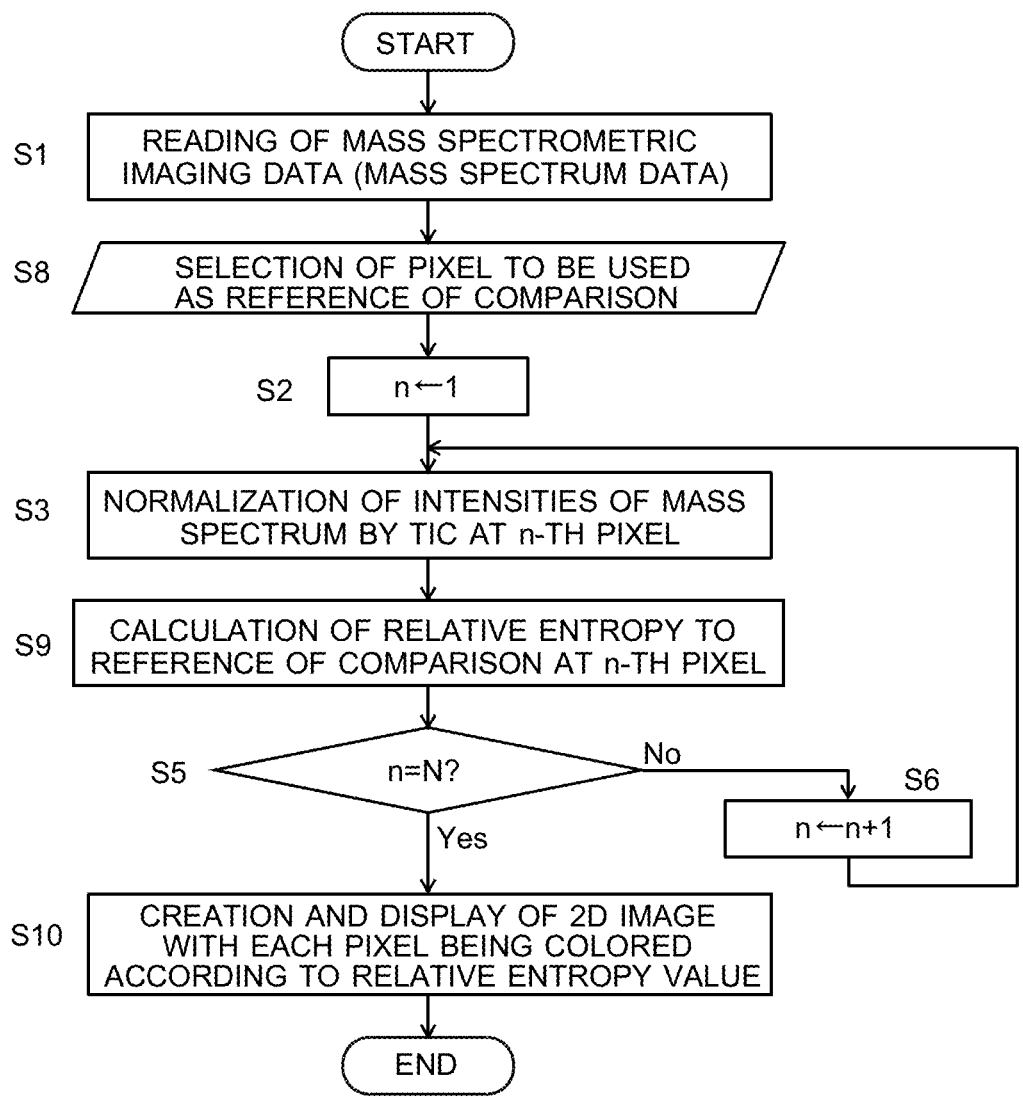

HE-STAINED IMAGE

MASS ANALYSIS IMAGE FOR m/z874.3

MASS SPECTRUM OF CANCER PART

MASS SPECTRUM OF NORMAL PART

TIC IMAGE (PRIOR ART)

ENTROPY IMAGE

WEIGHTED ENTROPY IMAGE

OPTICAL MICROSCOPIC IMAGE

HE-STAINED IMAGE

MASS SPECTROMETRIC IMAGE
FOR m/z 798.67
(AFTER NORMALIZATION)

TIC IMAGE (PRIOR ART)

ENTROPY IMAGE
WITH NO BINNING

ENTROPY IMAGE
WITH 2x2 BINNING

ENTROPY IMAGE
WITH 4x4 BINNING

RELATIVE ENTROPY IMAGE
WITH NO BINNING

RELATIVE ENTROPY IMAGE
WITH 2x2 BINNING

RELATIVE ENTROPY IMAGE
WITH 4x4 BINNING

METHOD AND SYSTEM FOR PROCESSING MASS ANALYSIS DATA

TECHNICAL FIELD

The present invention relates to a method and system for processing mass analysis data by the technique of mass spectrometric imaging, which includes the step of analyzing mass analysis data collected by performing a mass analysis for each of a plurality of micro areas in a two-dimensional area on a sample, and the step of outputting the result in the form of an image corresponding to the two-dimensional area.

BACKGROUND ART

In order to observe the morphology of a sample, such as a section of biological tissue, and simultaneously measure the distribution of the molecules existing in a specified area on the sample, a type of system called a mass microscope or an imaging mass spectrometer has been developed (for example, refer to Patent Documents 1-3 as well as Non-Patent Documents 1 and 2). These systems require no grinding or crushing of the sample and hence are capable of obtaining a distribution image (or mapping image) of the ions having a specific mass-to-charge ratio (m/z) included in any area specified on the sample based on a microscopic observation while almost completely maintaining the original morphology of the sample. Such systems are expected to be used, for example, to obtain distribution information of the proteins included in a living cell, particularly in the fields of biochemistry, medical care, pharmaceutical chemistry, and other applications.

It is important for an analysis operator to easily grasp desired information on a sample, such as the kind of substance that characterizes the sample or the distribution of the amount of that substance. To this end, an appropriate analysis processing should be performed on the collected mass spectrometric imaging data, and the result of the processing should be displayed in an appropriate form. If mass spectrometric imaging data are obtained for a two-dimensional area of a certain area on a sample, the data will include mass spectrum data of many measurement points (micro areas). Naturally, the amount of these data is enormous. Given this problem, various methods have been proposed to process such an enormous amount of data and extract significant information in an easy-to-understand fashion for the analysis operator.

In one method, for example, an integrated mass spectrum created by integrating the mass spectra of all measurement points is displayed on a display screen, on which the analysis operator can appropriately select a peak among the peaks appearing on the integrated mass spectrum. After selecting a peak, the analysis operator can display the intensity spatial distribution of that peak by using a commonly available mass-spectrum (MS) image display software product, such as BioMap (for example, refer to Non-Patent Document 3). Superimposing the spatial distributions of the intensity of two or more peaks in this manner provides information relating to the structure of a specified tissue and the mass-to-charge ratio of the main substance of the tissue.

Another type of method uses a multivariate analysis, such as a principal component analysis (PCA), independent component analysis (ICA) or factor analysis (FA) (for example, refer to Non-Patent Document 4). In the multivariate analysis, two or more substances forming close intensity spatial distributions gather by factors. Typically, a score and a loading are displayed in terms of each of the factors. In the method described in Non-Patent Document 4, the score is displayed as a two-dimensional spatial distribution, and the loading as a scatter diagram.

However, the previously described conventional methods have the following disadvantages: In an analysis method using MS image display software, when an analysis operator selects a peak on an integrated mass spectrum, the intensity spatial distribution for the mass-to-charge ratio corresponding to the selected peak is displayed. This method does not guarantee that the selected peak always corresponds to a substance that shows a spatially specific distribution. If a peak showing a spatially specific distribution must be located for each small area on a sample, the analysis operator needs to compare and superimpose the intensity spatial distributions of two or more peaks by trial and error. Consequently, the operator normally has to repeat the operation of displaying images for many peaks on the integrated mass spectrum, which requires a large amount of time and labor.

In the methods using a multivariate analysis, specialized knowledge and skills are required in many cases to determine the number of factors and interpret the loading value of each factor. In the case of PCA, a peak having a negative intensity may be included on the displayed mass spectrum of a main component and it is sometimes difficult to interpret the physical meaning of the result. Therefore, only a limited number of operators can conduct the analysis, which makes it difficult to efficiently perform the analysis and enhance the throughput. Another disadvantage of the PCA method exists in that the information obtained by this method is insufficient for determining the spatial distribution or content of a substance; the information relating to one substance is reflected in a plurality of main components, whereas the PCA method provides the spatial distribution of only one main component.

BACKGROUND ART DOCUMENT

Patent Document

Patent Document 1: JP-A 2007-66533
Patent Document 2: JP-A 2007-157353
Patent Document 3: JP-A 2007-257851

Non-Patent Document

Non-Patent Document 1: Kiyoshi Ogawa et al., "Kenbi Shitsuryou Bunseki Souchi No Kaihatsu," ("Research and Development of Mass Microscope") *Shimadzu Review*, Shimadzu Corporation, Mar. 31, 2006, vol. 62, nos. 3•4, pp. 125-135

Non-Patent Document 2: Takahiro Harada et al., "Kenbi Shitsuryou Bunseki Souchi Ni Yoru Seitai Soshiki Bunseki," ("Biological Tissue Analysis Using Mass Microscope") *Shimadzu Review*, Shimadzu Corporation, Apr. 24, 2008, vol. 64, nos. 3•4, pp. 139-146

Non-Patent Document 3: "MS Imaging Gijutsu Ni Yoru Byouri Soshiki Seppen Jou Ni Okeru Biomarker No Tansaku," ("Search for Biomarkers on Pathological Samples Using MS Imaging Technology"), [online], Shimadzu Corporation, [Oct. 8, 2010], Internet Non-Patent Document 4: Morinaga et al., "Development of the Software Using Principal Component Analysis for MS Imaging Data," *Abstract of the 57th Annual Conference on Mass Spectrometry* 2009, the Mass Spectrometry Society of Japan, May 1, 2009

DISCLOSURE OF THE INVENTION

Problem to be Solved by the Invention

The present invention has been developed to solve the aforementioned problems, and the objective thereof is to provide a mass analysis data processing method and system capable of efficiently processing a large amount of data collected by an imaging mass analysis to present significant information for the analysis of the tissue structure of a biological sample or other objects in an intuitively understandable form for analysis operators.

Means for Solving the Problems

The first aspect of the present invention aimed at solving the aforementioned problem provides a mass analysis data processing method for processing data collected by performing a mass analysis for each of a plurality of micro areas set in a two-dimensional area on a sample, including the steps of:

a) normalizing, for each of the micro areas, intensity information of mass spectrum data corresponding to the micro area;

b) calculating entropy at each micro area based on the mass spectrum data after normalization; and c) coloring the micro areas by giving each micro area a display color corresponding to an entropy value calculated for that micro area, for creating a colored two-dimensional image corresponding to the aforementioned two-dimensional area, and for displaying the created image.

The second aspect of the present invention aimed at solving the aforementioned problem provides a system for carrying out the mass analysis data processing method according to the first aspect of the present invention. That is to say, the second aspect of the present invention is a mass analysis data processing system for processing data collected by performing a mass analysis for each of a plurality of micro areas set in a two-dimensional area on a sample, including:

a) a normalizing processor for normalizing, for each of the micro areas, intensity information of mass spectrum data corresponding to the micro area;

b) an entropy calculator for calculating entropy at each micro area based on the mass spectrum data after normalization; and c) a display information creator for coloring the micro areas by giving each micro area a display color corresponding to an entropy value determined for that micro area, for creating a colored two-dimensional image corresponding to the aforementioned two-dimensional area, and for displaying the created image on a display screen.

In the method and system for processing mass analysis data according to the present invention, the "entropy" can be typically defined as the sum of the product of the intensity value at each mass-to-charge ratio and a logarithm (either a natural or common logarithm) of that intensity value in a mass spectrum over the entire range of the mass-to-charge ratios.

In information theory, entropy is used as an index of the amount of information. If entropy is introduced for the mass spectrum data for each micro area (for each pixel in the case of an image), the entropy will be larger as the number of significant peaks is greater. A "significant" peak is a peak that can characterize the micro area concerned. For example, a given peak will not be regarded as "significant" if many other peaks having comparable intensities exist over the entire range of the mass-to-charge ratios. A study by the present inventors has revealed that the entropy as defined for a mass spectrum does not simply reflect the number of kinds of contained substances; it reflects the degree of complexity of the compositional ratio of the substances. The entropy will be relatively small if the compositional of the substances in the micro area is relatively simple, or in other words, as the composition of those substances is biased. Accordingly, it is probable that, for a sample originating from a living organism, the distribution of the entropy value obtained from the mass spectrum data for each micro area reflects the spatial distribution of a substance associated with the functions or effects of the cell, an aggregation of the cells or the like.

The method and system for processing mass analysis data according to the present invention is based on such an idea. That is to say, in the first step, the normalizing processor performs a normalizing operation as a pre-process for entropy calculation, in which the intensity at each of the mass-to-charge ratios in the mass spectrum corresponding to one micro area are normalized for each micro area so that the sum of the intensities will be one. This normalization eliminates the influences of the difference in the absolute content of the substances between the micro areas and enables the comparison of the entropy values. In the second step, the entropy calculator calculates entropy for each micro area, using the mass spectrum data after the normalization. In the third step, the display information creator selects the display color of each micro area, for example, by comparing the entropy value of the micro area with a previously set color scale, and displays a two-dimensional color image with each pixel in the corresponding color. The displayed image visualizes the two-dimensional distribution of the entropy of the individual micro areas.

In the case where the sample is a biological tissue, a substance having a large mass-to-charge ratio tends to decrease (i.e. be decomposed into substances of smaller mass-to-charge ratios) due to the decomposition of the substance by enzymatic digestion during the pre-processing of the sample or the dissociation of the sample components by the action of a laser beam used in the ion source during the mass-analyzing process. Taking this into account, in a preferable mode of the mass analysis data processing system according to the present invention, the normalizing processor performs the normalization in such a manner that the intensity information of the mass spectrum data is weighted according to the mass-to-charge ratio.

Specifically, it is preferable to give a larger weight to an ion having a larger mass-to-charge ratio. The weight values can be appropriately specified, for example, by a preliminary experiment, based on the kind of sample, the pre-processing method, the configuration of the mass spectrometer, and other factors. Such a weighting operation reduces the influence of the decomposition of a substance having a large mass-to-charge ratio caused by the aforementioned factors. As a result, the spatial distribution of the substance associated with the previously mentioned functions or effects will be more clearly reflected.

In the case of determining the distribution of the portions of the sample whose functions or effects are identical or similar to those of a specific portion that can be recognized, for example, by using an optical microscopic image of the sample, it is possible to make the distribution easier to visually recognize by using the entropy of the specific portion as a reference value and showing the entropies of the other portions as the relative values to the reference value.

Accordingly, in one mode of the mass analysis data processing system according to the present invention:

a reference selector for selecting one of the micro areas as a reference of comparison is further provided; and the entropy calculator calculates relative entropy of each micro area with reference to the entropy of a micro area selected as the reference of comparison by the reference selector.

The reference selector may include: a display unit having a display screen for displaying an optical microscopic image of a sample, a mass analysis result image showing the intensity distribution at a specific mass-to-charge ratio, or other types of images; and an operation unit, such as a pointing device, for allowing a user to specify a point on the displayed image. It is also possible to use an image-recognition technique to automatically extract, from an optical microscopic image of the sample or a mass analysis result image, a portion satisfying predetermined conditions and select the micro area corresponding to the extracted portion as the reference of comparison.

Depending on the kind of sample, the size of the portion of interest or other factors, it may be more preferable to collectively process the mass spectrum data of a plurality of adjacent micro areas, than to separately process the data of each micro area defined as the smallest unit of the mass analysis, in order to make the portion of interest more apparent when visualized. Accordingly, in one possible mode of the present invention, the mass analysis data processing system further includes a binning processor for performing, before the normalization by the normalizing processor, a binning process in which the mass spectrum data of a plurality of micro areas adjacent to or neighboring with each other within the two-dimensional area are added or averaged, Effect of the Invention With the method and system for processing mass analysis data according to the present invention, a large amount of data collected by an imaging mass analysis can be efficiently processed to create information from which the spatial distribution of a substance contained in a sample can be easily and intuitively understood, and this information can be presented to an analysis operator. Particularly, the method and system for processing mass analysis data according to the present invention can be used to examine the biological tissue of a man or animal and correctly distinguish between the normal part of the sample and a lesion part (e.g. a cancerous part) in which a certain kind of substance specifically exists.

By the method and system for processing mass analysis data according to the present invention, the processing time is reduced and the analysis throughput is improved, since it is unnecessary to repeat the conventional trial-and-error process of selecting a peak or peaks on an integrated mass spectrum, or to perform a peak-extracting process which is normally required in a multivariate analysis. Another advantage exists in that the operational load on the analysis operator is reduced, since no such specialized knowledge or skills as required in the method using a multivariate analysis are needed to analyze data or interpret the result of the analysis.

BRIEF DESCRIPTION OF THE DRAWINGS

"The file of this patent contains at least one drawing executed in color. Copies of this patent with color drawings will be provided by the Office upon request and payment of the necessary fee".

FIG. 3 is a flowchart showing a data-processing procedure in one variation of the imaging mass spectrometer of the present embodiment.

BEST MODE FOR CARRYING OUT THE INVENTION

Figure 1:
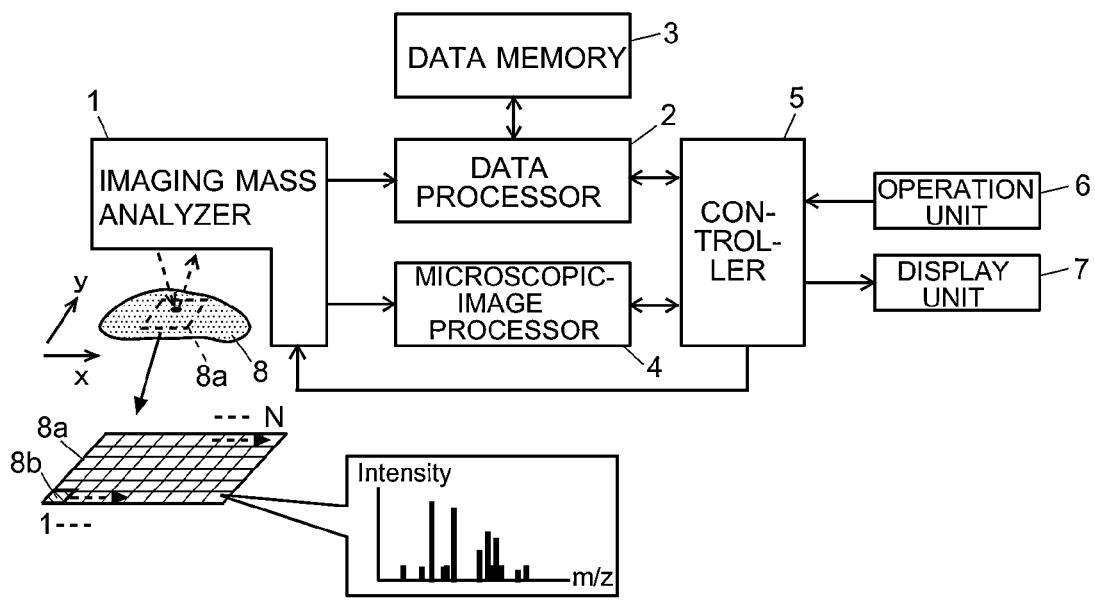
FIG. 1 is a schematic configuration diagram of one embodiment of an imaging mass spectrometer using a mass analysis data processing system according to the present invention.

One embodiment of an imaging mass spectrometer for carrying out the mass analysis data processing method according to the present invention is hereinafter described with reference to the attached drawings. FIG. 1 is a schematic configuration diagram of the imaging mass spectrometer in accordance with the present embodiment.

This imaging mass spectrometer includes: an imaging mass analyzer 1 for performing a microscopic observation of a two-dimensional measurement area 8a on a sample 8 and for carrying out an imaging mass analysis within the area 8a; a data processor 2 for analyzing mass spectrum data collected by the imaging mass analyzer 1; a data memory 3 for storing mass spectrum data; a microscopic-image processor 4 for processing image signals obtained with the imaging mass analyzer 1 to create a microscopic image; a controller 5 for controlling these functional components; and an operation unit 6 as well as a display unit 7, both being connected to the controller 5.

Though not shown in the figure, the imaging mass analyzer 1 includes a matrix-assisted laser desorption ionizer (MALDI), an ion transport optical system, an ion trap, a time-of-flight mass analyzer, an ion detector and other elements, as described in Non-Patent Document 1 or 2, to perform a mass analysis for each micro area 8b having a predetermined size over a specific range of mass-to-charge ratios in each of the x and y directions. The imaging mass analyzer 1 further includes a stage driver for precisely moving a stage (not shown), with the sample 8 placed thereon, along the two axes of x and y. With this mechanism, mass spectrum data for a given area of any size can be collected by performing a mass analysis every time the sample 8 is moved stepwise by a predetermined width. At least a portion of the functions of the controller 5, data processor 2, data memory 3, microscopic-image processor 4 and other components can be realized by running a dedicated processing and controlling software program installed on a personal computer.

The imaging mass spectrometer of the present embodiment is characterized by a data processing performed in the data processor 2 to analyze a large amount of mass analysis imaging data collected by the imaging mass analyzer 1 and display the result of the analysis on the screen of the display unit 7. (The "mass spectrometric imaging data" is a collection of N sets of mass-spectrum data, with each set of the mass spectrum data obtained from one micro area.) One example of this characteristic data processing is hereinafter described by means of FIG. 2, which is a flowchart showing the data-processing procedure.

In the imaging mass analyzer 1, a mass spectrum data is obtained for each of the micro areas 8b formed by subdividing, in both the x and y directions, the two-dimensional measurement area 8a previously set on the sample 8, as shown in FIG. 1. It is herein assumed that there are a total of N micro areas in the two-dimensional measurement area 8a. A mass spectrum data is a set of data forming a mass spectrum showing the intensity signal over a predetermined range of mass-to-charge ratios.

The length of one side of the micro area 8b is normally determined by the moving step of the stage carrying the sample 8. As will be described later, the display color of each micro area 8b on a colored two-dimensional image is chosen by a data processing based on the mass spectrum data obtained at the micro area 8b concerned. This means that, as far as image processing (such as coloring) is concerned, the micro area is the smallest unit and hence synonymous with the "pixel." Accordingly, the micro areas will be hereinafter called the "pixels."

When a command for initiating the data processing is given, the data processor 2 accesses the data memory 3 to read the mass spectrometric imaging data to be processed, i.e. all the mass spectrum data obtained for each pixel (Step S1). In the present case, the mass spectrum data collected from the N micro areas are read.

Next, parameter n is initialized to 1 (Step S2), and the intensity of the mass spectrum at the n-th pixel is normalized (Step S3). Specifically, the total ion current (TIC) is calculated by the following equation:

$$TIC = \Sigma p(i) \qquad (1),$$

where $p(i)$ is the intensity signal at the i-th sample point (mass-to-charge ratio) counted along the axis of the mass-to-charge ratio in the mass spectrum, and $\Sigma$ is the operator for calculating the sum of $p(i)$ from i=1 to M (which is the maximum value of the sample point). That is to say, equation (1) gives the sum of the ion intensity measured at each mass-to-charge ratio over the entire range of mass-to-charge ratios in the mass spectrum. Using the obtained value of TIC, a normalized intensity signal $p'(i)$ is calculated by the following equation:

$$p'(i) = p(i)/TIC \qquad (2).$$

The sum of $p'(i)$ calculated by equation (2) for i=1 to M will be one.

Next, the data processor 2 calculates entropy $S_n(n)$ at the n-th pixel (Step S4). Specifically, this entropy is calculated by the following equation using the normalized intensity signals $p'(i)$ calculated by equation (2):

$$S_n(n) = -\Sigma p'(i) \cdot \log(p'(i)) \qquad (3).$$

In this equation, the natural logarithm (ln) may be used in place of the common logarithm (log).

After the entropy is calculated, whether the parameter n has reached N (the total number of pixels) is checked to determine whether the processes of all the pixels have been completed (Step S5). If n is still less than N, n is increased by one (Step S6) and then the operation returns to Step S3. By repeating the processes of Steps S3 through S6 N times, the entropy is computed for all the pixels.

Subsequently, the controller 5 refers to a color scale in which the correspondence between the value (or range) of the entropy and the display color is specified, creates a two-dimensional image in which each portion corresponding to one pixel is shown in the display color selected according to the value of the entropy $S_n(n)$ calculated for that pixel, and displays this image on the screen of the display unit 7 (Step S7). It is also possible to output the image through a printer or other devices. As a result of such a process, an entropy image showing the distribution of the entropy calculated from the mass analysis data for each pixel is obtained.

In the previously described method, a simple normalization and entropy calculation were performed on the mass spectrum data of each pixel. This method can be further modified as follows.

[Weighted Entropy]

Figure 2:
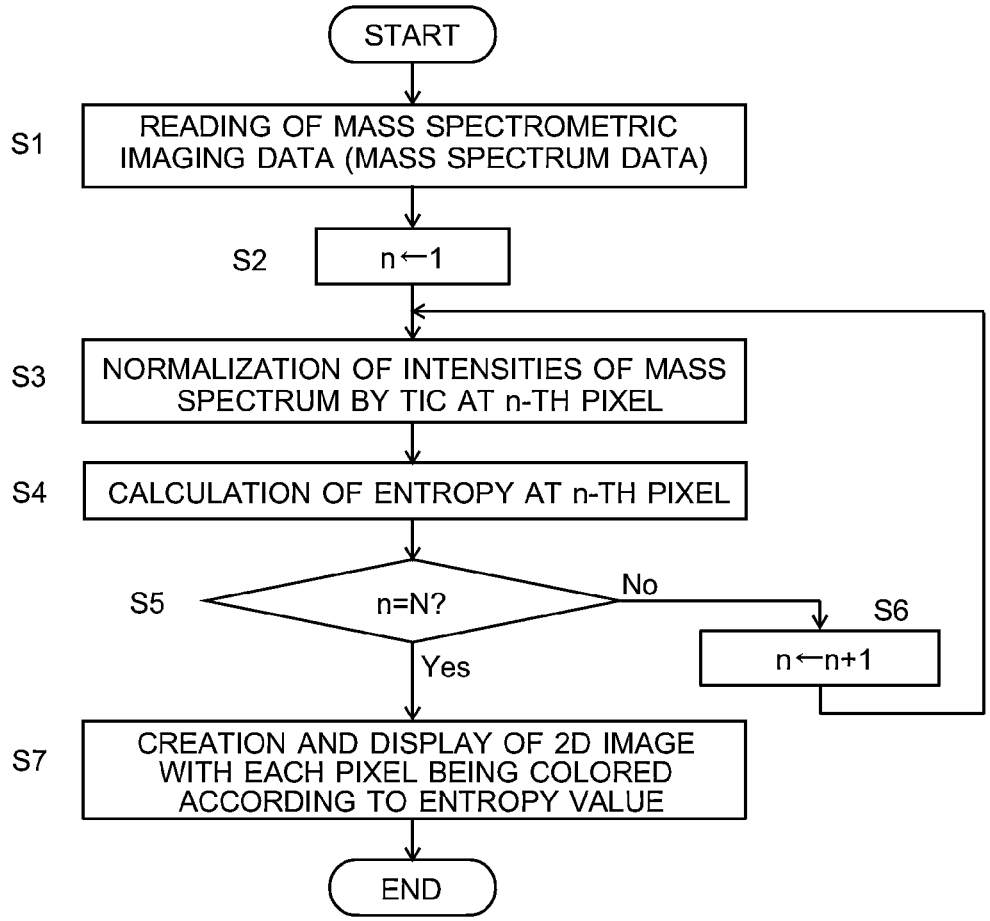
FIG. 2 is a flowchart showing a data-processing procedure in the imaging mass spectrometer of the present embodiment.

That is to say, the intensity signals of the mass spectrum obtained at each pixel may be weighted according to the mass-to-charge ratio before the calculation of the entropy (or relative entropy, which will be described later). In general, a substance that exists in a biological sample and has a relatively high molecular weight easily breaks into substances of lower masses due to the decomposition by enzymatic digestion or the dissociation by the laser used for the ionization of the sample in the mass spectrometer. Taking such a decomposition of the substance into account, it is preferable to perform the weighting in such a manner that a larger weight is given to an ion having a larger mass-to-charge ratio. In this case, the process of Step S3 in FIG. 2 is modified so that the intensity signals are weighted by the following equation before the normalization is performed:

$$p_w(i) = m(i) \cdot p(i) \qquad (4)$$

where $m(i)$ is the mass-to-charge ratio (m/z) at the i-th sample point.

Accordingly, equations (1) and (2) will be respectively changed as follows:

$$TIC_w = \Sigma p_w(i),$$

$$p_w'(i) = p_w(i)/TIC_w.$$

Equation (3) in Step S4 will also be changed as follows:

$$S_w(n) = -\Sigma p_w'(i) \cdot \log(p_w'(i)) \qquad (5).$$

This equation gives the weighted entropy $S_w(n)$ for the n-th pixel. The other processes are the same as already explained.

[Relative Entropy]

If the purpose of the analysis is to determine the distribution or spread of one or more portions similar to a specific portion in the two-dimensional measurement area 8a of the sample 8, it is recommendable to use relative entropy with the entropy of a specific pixel as the reference value. FIG. 3 is a flowchart showing the data-processing procedure in the case of using the relative entropy. The steps in which the same processes as already shown in the flowchart of FIG. 2 are performed are denoted by the same step numbers.

In this case, for example, a user (operator) visually checks an optical microscopic image of a sample on the screen of the display unit 7 and operates the operation unit 6 to select a pixel which should serve as the specified portion and be used as the reference of comparison (Step S8). The user can select any portion as the specified portion. For example, if the target of observation is a cancerous part in a biological tissue, any pixel included in a visually recognizable portion of the cancer can be selected as the specified portion. In Step S9, which substitutes for Step S4 in FIG. 2, the relative entropy to the entropy value of the selected pixel is calculated in place of the absolute entropy.

For example, for the n-th pixel, the relative entropy $S_r(n)$, or more strictly, an average of the relative entropy is calculated by the following equation:

$$S_r(n) = \{-\Sigma p'(i) \cdot \log(p'(i)/q'(i)) - \Sigma q'(i) \cdot \log(q'(i)/p'(i))\}/2 \quad (6),$$

where $q'(i)$ is the intensity signal (normalized by using TIC) of the i-th sample point at the pixel selected as the reference of comparison. The other processes are the same as already described.

Instead of allowing a user to select a pixel as the reference of comparison, the system may automatically extract a portion of interest by the image-recognition processing of an optical microscopic image or other methods, and select the extracted pixel as the reference of comparison.

[Addition of Binning Processing]

As another variation of the present embodiment, a binning process may be performed on the mass spectrum of at a plurality of pixels. That is to say, the intensity signals obtained at a plurality of pixels located next to or adjacent to each other within the two-dimensional measurement area 8a may be integrated or averaged for each mass-to-charge ratio to apparently enlarge the pixel size to some extent, e.g. four or sixteen times, before the mass spectrum data are normalized and the absolute or relative entropy is calculated in the previously described manner. It is naturally possible to use weighted entropy. Adding the binning process is effective for reducing the measurement noise or lessening variations among the neighboring pixels.

EXAMPLES

Examples of actual measurements using the imaging mass spectrometer of the present embodiment are hereinafter described with reference to FIGS. 4A-8C.

First Example of Actual Measurement

Figure 4A:
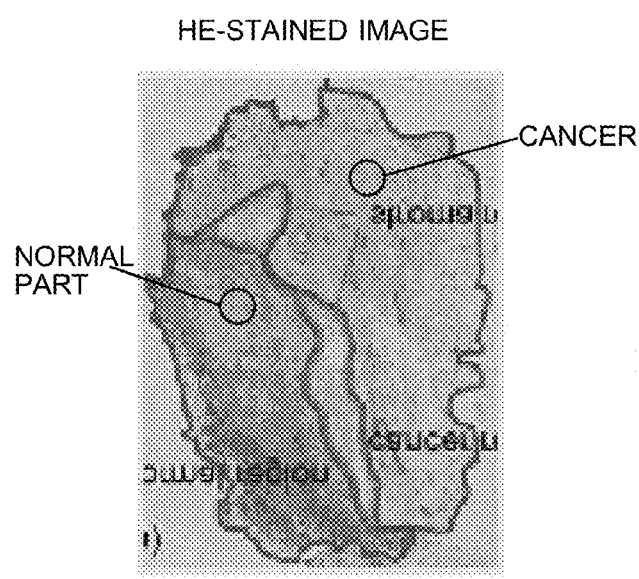
FIGS. 4A-4D show one example of the actual measurement performed with the imaging mass spectrometer of the present embodiment.
Figure 4B:
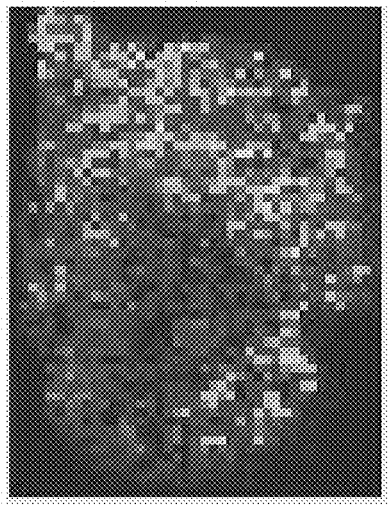
Figure 4C:
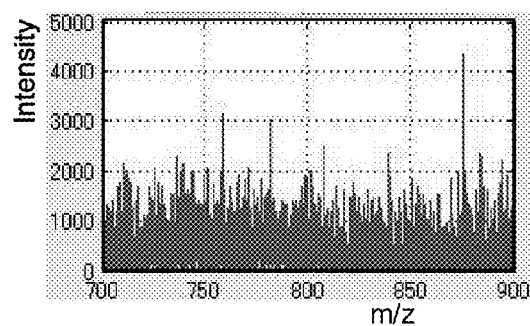
Figure 4D:
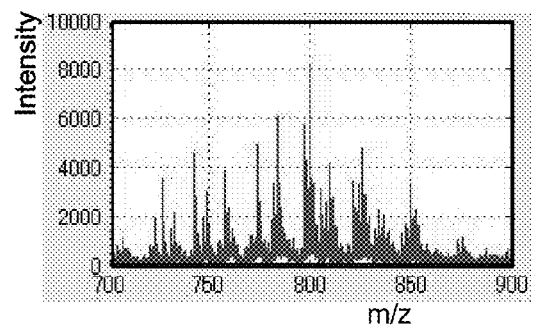

The result of a measurement for a sample of a human liver metastasis from a colon cancer is hereinafter described by means of FIGS. 4A-4D and 5A-5C. FIG. 4A is an optical microscopic image of the sample stained with hematoxilin-eosin (HE). FIG. 4B is a mass analysis result image for m/z874.3, which is detected in a cancerous part. Naturally, this mass-to-charge ratio cannot be known beforehand in the case of measuring an unknown sample. FIG. 4C is a mass spectrum obtained at a pixel included in the cancer site shown in FIG. 4A. FIG. 4D is a mass spectrum obtained at a pixel included in the normal site shown in FIG. 4A.

Figure 5A:
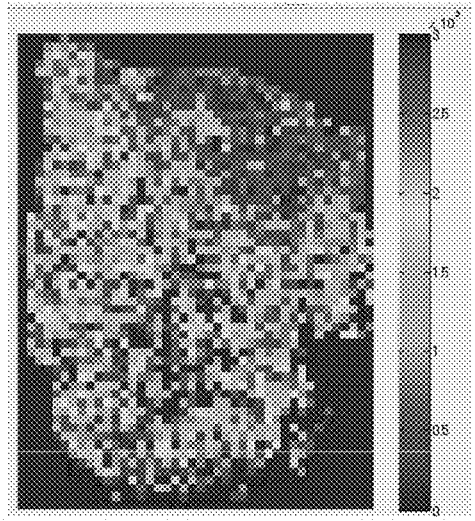
FIGS. 5A-5C show one example of the actual measurement performed with the imaging mass spectrometer of the present embodiment.
Figure 5B:
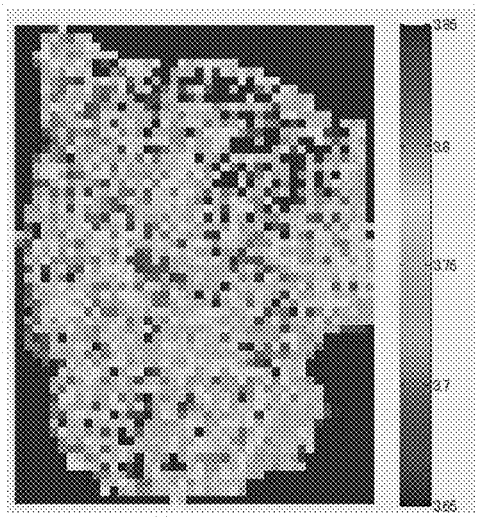
Figure 5C:
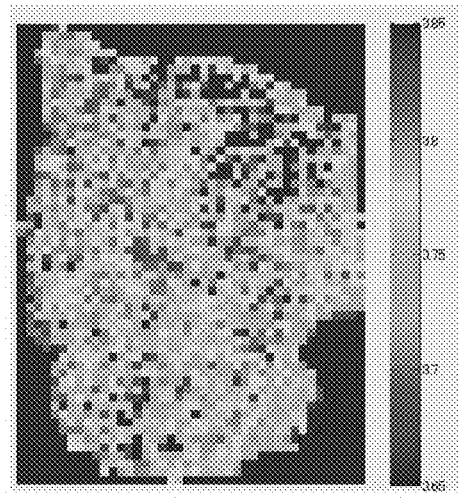

FIG. 5A is a TIC image in which the TIC value of each pixel is simply represented according to a color scale. FIG. 5B is an entropy image created according the process steps shown in FIG. 2. FIG. 5C is a weighted entropy image created by a process in which the normalization of the mass-spectrum intensities was performed after a weighting operation in which a larger weight was given to a larger mass-to-charge ratio (m/z).

In the present example, both the TIC and the entropy are smaller in the cancerous part than in the normal part. Generally speaking, when the TIC is small, there are a large number of peaks in the mass spectrum and the entropy tends to be high. By contrast, in the present example, since both the TIC and the entropy are small, the spatial distribution of the cancerous part can be clearly located on the entropy image or the weighted entropy image. Accordingly, it can be said that whether or not the portion of interest (e.g. the cancerous part in the present case) can be recognized on a TIC image depends on the kind of sample or the kind of substance forming the portion of interest, whereas the portion of interest can be recognized on an entropy image irrespective of the kind of sample or substance.

Second Example of Actual Measurement

Figure 6A:
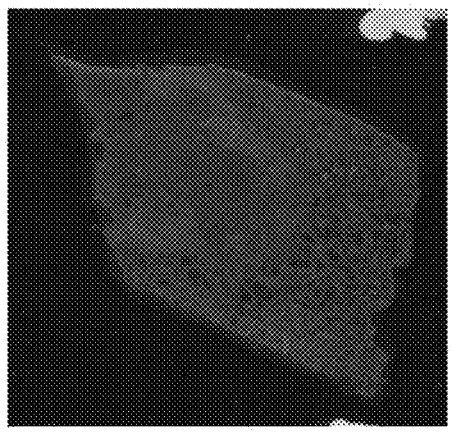
FIGS. 6A-6D show one example of the actual measurement performed with the imaging mass spectrometer of the present embodiment.
Figure 6B:
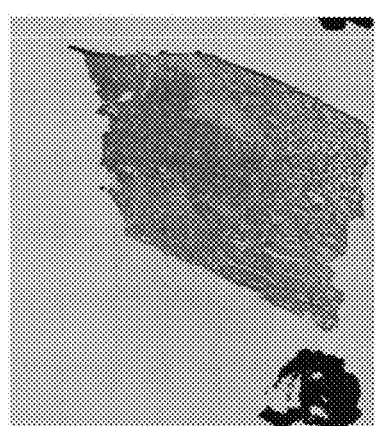
Figure 6C:
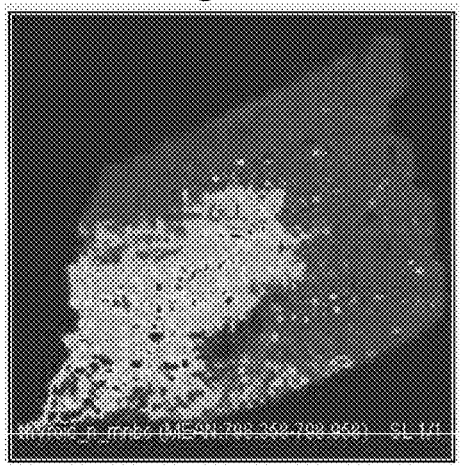
Figure 6D:
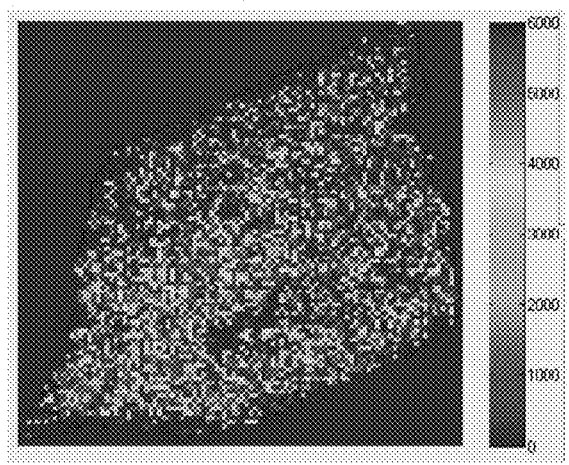

The result of a measurement for a sample of a human thyroid cancer is hereinafter described by means of FIGS. 6A-6D, FIGS. 7A-7C and FIGS. 8A-8C. FIG. 6A is an optical microscopic image of this sample. FIG. 6B is an optical microscopic image of the same sample stained with HE. FIG. 6C is a mass analysis result image for m/z798.67, which is detected in the cancerous part. FIG. 6D is a TIC image. For FIG. 6C, normalization was performed so that the TIC at each pixel would be 1. It is difficult to discern the cancerous part on the TIC image shown in FIG. 6D. The difference in the position and orientation of the sample between FIG. 6A/6B and FIG. 6C/6D is merely due to a positional shift which occurred when placing the sample.

Figure 7A:
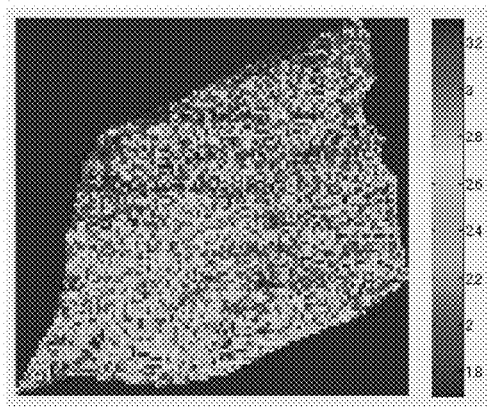
FIGS. 7A-7C show one example of the actual measurement performed with the imaging mass spectrometer of the present embodiment.
Figure 7B:
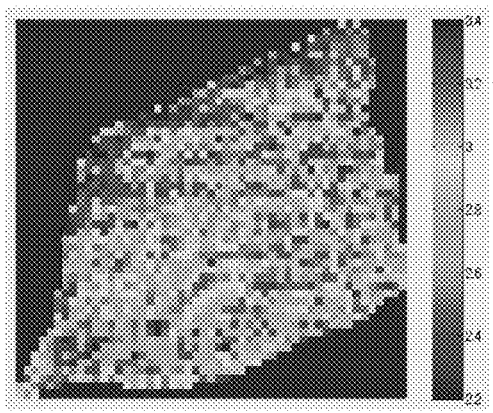
Figure 7C:
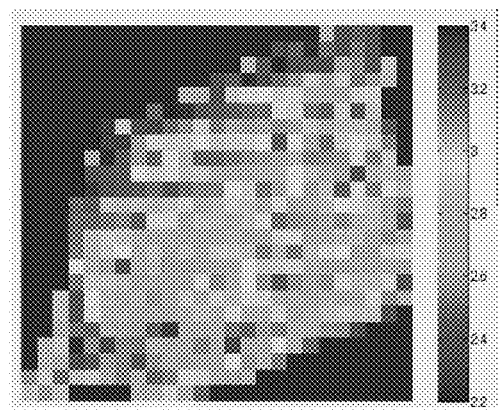

FIG. 7A is an entropy image (with no binning), while FIG. 7B is an entropy image with 2×2 binning, which shows the distribution of the entropy calculated for a mass spectrometric imaging data created by replacing the mass spectrum of each pixel with an averaged mass spectrum of 2×2 pixels. Similarly, FIG. 7C is an entropy image with 4×4 binning, which shows the distribution of the entropy calculated for a mass spectrometric imaging data created by replacing the mass spectrum of each pixel with an averaged mass spectrum of 4×4 pixels. In any of these images, the cancerous part at the bottom left can be clearly recognized as a region of small entropies, and this region becomes more distinct as a result of the binning.

Figure 8A:
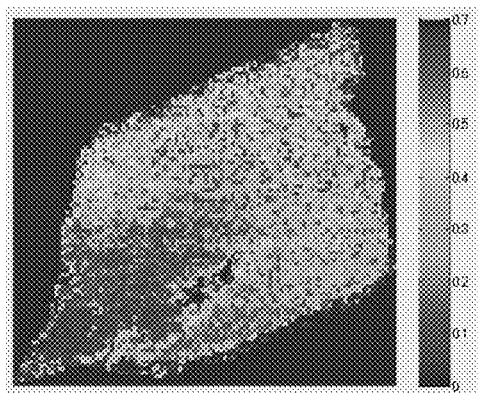
FIGS. 8A-8C show one example of the actual measurement performed with the imaging mass spectrometer of the present embodiment.
Figure 8B:
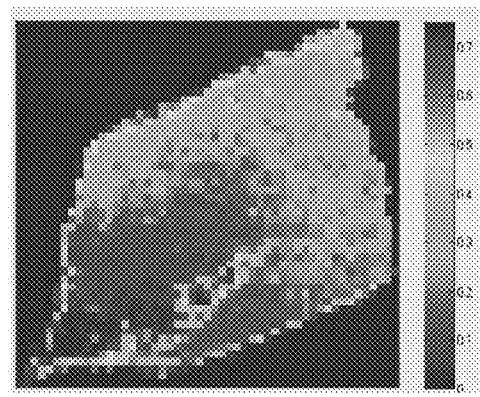
Figure 8C:
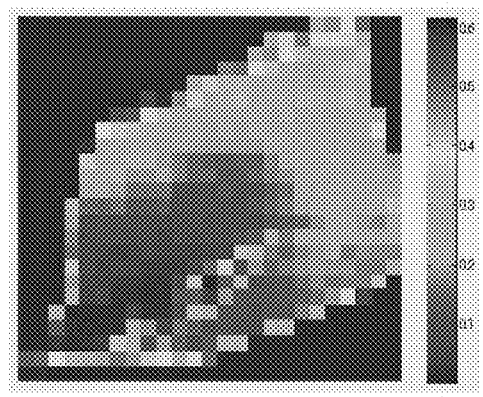

FIG. 8A is a relative entropy image (with no binning) in which one pixel included in the cancerous part was specified as the reference of comparison. FIG. 8C is a relative entropy image with 2×2 binning. FIG. 8C is a relative entropy image with 4×4 binning. These images also clearly show the cancerous part as a region whose relative entropy is small (i.e. a region similar to the reference part in terms of the degree of compositional complexity). However, in these images, the boundary between the peripheral portion of the sample and the outer space is excessively emphasized as a result of the binning. This result suggests that the binning is not always effective for distinctly showing the portion of interest; in some cases it is better to avoid performing the binning.

The results of the actual measurements described to this point have confirmed that by the data-processing method and system according to the present invention the region of a cancerous part in a biological sample can be identified. Such a region cannot be practically identified on a TIC image. The identification of the cancerous part is possible even on a simple entropy image. However, it is further effective to use weighted entropy or relative entropy using a specific portion (pixel) as the reference or combine the entropy or relative entropy and the technique of pixel binning in which the information of a plurality of adjacent pixels is combined into one piece of information.

It should be noted that the previous embodiment is a mere example of the present invention, and any change, modification or addition appropriately made within the spirit of the present invention will naturally fall within the scope of claims of the present patent application.

EXPLANATION OF NUMERALS

1 . . . Imaging Mass Analyzer
2 . . . Data Processor

3 ... Data Memory
4 ... Microscopic-Image Processor
5 ... Controller
6 ... Operation Unit
7 ... Display Unit
8 ... Sample
8a ... Two-Dimensional Measurement Area
8b ... Micro Area (Pixel)

The invention claimed is:

1. A mass analysis data processing method for processing data collected by performing a mass analysis for each of a plurality of micro areas set in a two-dimensional area on a sample, comprising the steps of:
 a) normalizing, for each of the micro areas, intensity information of mass spectrum data corresponding to the micro area;
 b) calculating entropy at each micro area based on the mass spectrum data after normalization; and
 c) coloring the micro areas by giving each micro area a display color corresponding to the entropy calculated at each micro area, for creating a colored two-dimensional mass analysis image corresponding to the aforementioned two-dimensional area, and for displaying the created image.

2. A mass analysis data processing system for processing data collected by performing a mass analysis for each of a plurality of micro areas set in a two-dimensional area on a sample, comprising:
 a) a normalizing processor for normalizing, for each of the micro areas, intensity information of mass spectrum data corresponding to the micro area;
 b) an entropy calculator for calculating entropy at each micro area based on the mass spectrum data after normalization; and
 c) a display information creator for coloring the micro areas by giving each micro area a display color corresponding to the entropy calculated at each micro area, for creating a colored two-dimensional mass analysis image corresponding to the aforementioned two-dimensional area, and for displaying the created image on a display screen.

3. The mass analysis data processing system according to claim 2, wherein the entropy calculator calculates the entropy by adding a product of an intensity value at each mass-to-charge ratio and either a natural or common logarithm of that intensity value in a mass spectrum over an entire range of the mass-to-charge ratios.

4. The mass analysis data processing system according to claim 2, wherein the normalizing processor performs the normalization in such a manner that intensity information of the mass spectrum data is weighted according to the mass-to-charge ratio.

5. The mass analysis data processing system according to claim 2, wherein:
 a reference selector for selecting one of the micro areas as a reference of comparison is further provided; and
 the entropy calculator calculates relative entropy of each micro area with reference to the entropy of a micro area selected as the reference of comparison by the reference selector.

6. The mass analysis data processing system according to claim 2, further comprising a binning processor for performing, before the normalization by the normalizing processor, a binning process in which the mass spectrum data of a plurality of micro areas adjacent to or neighboring with each other within the two-dimensional area are added or averaged.

* * * * *